US010702056B2

(12) United States Patent
Xi et al.

(10) Patent No.: US 10,702,056 B2
(45) Date of Patent: Jul. 7, 2020

(54) LIGHT-EMITTING ORAL CARE IMPLEMENT AND METHOD OF FORMING THE SAME

(71) Applicant: Colgate-Palmolive Company, New York, NY (US)

(72) Inventors: Wen Jin Xi, Shanghai (CN); Bo Zhang, Yangzhou (CN); Guang Sheng Guo, Yangzhou (CN)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 16/061,381

(22) PCT Filed: Dec. 14, 2015

(86) PCT No.: PCT/CN2015/097247
§ 371 (c)(1),
(2) Date: Jun. 12, 2018

(87) PCT Pub. No.: WO2017/100974
PCT Pub. Date: Jun. 22, 2017

(65) Prior Publication Data
US 2018/0360202 A1    Dec. 20, 2018

(51) Int. Cl.
*A46D 1/00*     (2006.01)
*A46D 3/00*     (2006.01)
(Continued)

(52) U.S. Cl.
CPC .......... *A46B 15/0036* (2013.01); *A46B 3/005* (2013.01); *A46B 9/04* (2013.01);
(Continued)

(58) Field of Classification Search
CPC combination set(s) only.
See application file for complete search history.

(56) References Cited

U.S. PATENT DOCUMENTS 5,030,093 A    7/1991   Mitnick
5,061,106 A    10/1991  Kent
(Continued)

FOREIGN PATENT DOCUMENTS

CN            102273812 A        12/2011
CN         2014/054911            4/2014
(Continued)

OTHER PUBLICATIONS

International Search Report and Written Opinion of the International Searching Authority in International Application No. PCT/CN2015/097247, dated Sep. 21, 2016.

*Primary Examiner* — Scott Luan

(57) ABSTRACT

A light-emitting oral care implement includes a light delivery unit that includes a passageway through a body of the oral care implement and a tuft comprising a plurality of filaments located in the passageway, each of the filaments having a core component and a sheath component. The core component may have a transmittance that is greater than the transmittance of the sheath component. The core component may include a base portion that protrudes from a lower end of the sheath component, the base portion forming an anchor portion of the tuft that anchors the tuft to the body of the oral care implement. Furthermore, the oral care implement may include a light source that transmits lights through the anchor portion of the tuft and through the core components for transmittance from the filaments at a location above a front surface of the body.

17 Claims, 13 Drawing Sheets

(51) Int. Cl.
  *A61N 5/06* (2006.01)
  *A46B 15/00* (2006.01)
  *A46B 9/04* (2006.01)
  *A46B 3/00* (2006.01)

(52) U.S. Cl.
  CPC .............. *A46D 1/023* (2013.01); *A46D 3/00* (2013.01); *A61N 5/062* (2013.01); *A46B 2200/1066* (2013.01); *A61N 2005/0606* (2013.01)

(56) References Cited

U.S. PATENT DOCUMENTS

| | | | |
|---|---|---|---|
| 5,313,909 A | 5/1994 | Tseng et al. | |
| 5,770,307 A | 6/1998 | Rackley et al. | |
| 6,862,771 B1 * | 3/2005 | Muller | A46B 15/0002 15/105 |
| 7,223,281 B2 | 5/2007 | Tuchin | |
| 8,429,783 B2 | 4/2013 | Russell et al. | |
| 8,984,699 B2 | 3/2015 | Russell et al. | |
| 2008/0131834 A1 | 6/2008 | Shepherd et al. | |
| 2008/0276393 A1 * | 11/2008 | Russell | A46B 7/00 15/105 |
| 2011/0256509 A1 | 10/2011 | Russell et al. | |
| 2015/0164212 A1 | 6/2015 | Russell et al. | |
| 2015/0359326 A1 * | 12/2015 | Chan | A46D 1/0207 15/167.1 |
| 2018/0199819 A1 | 7/2018 | Yoshida et al. | |

FOREIGN PATENT DOCUMENTS

| | | |
|---|---|---|
| CN | 105011554 A | 11/2015 |
| GB | 2325401 A | 11/1998 |
| WO | 2000/007482 | 2/2000 |
| WO | 2007/093860 | 8/2007 |
| WO | 2007/109136 | 9/2007 |
| WO | 2007/111703 | 10/2007 |
| WO | 2013/119776 | 8/2013 |

* cited by examiner

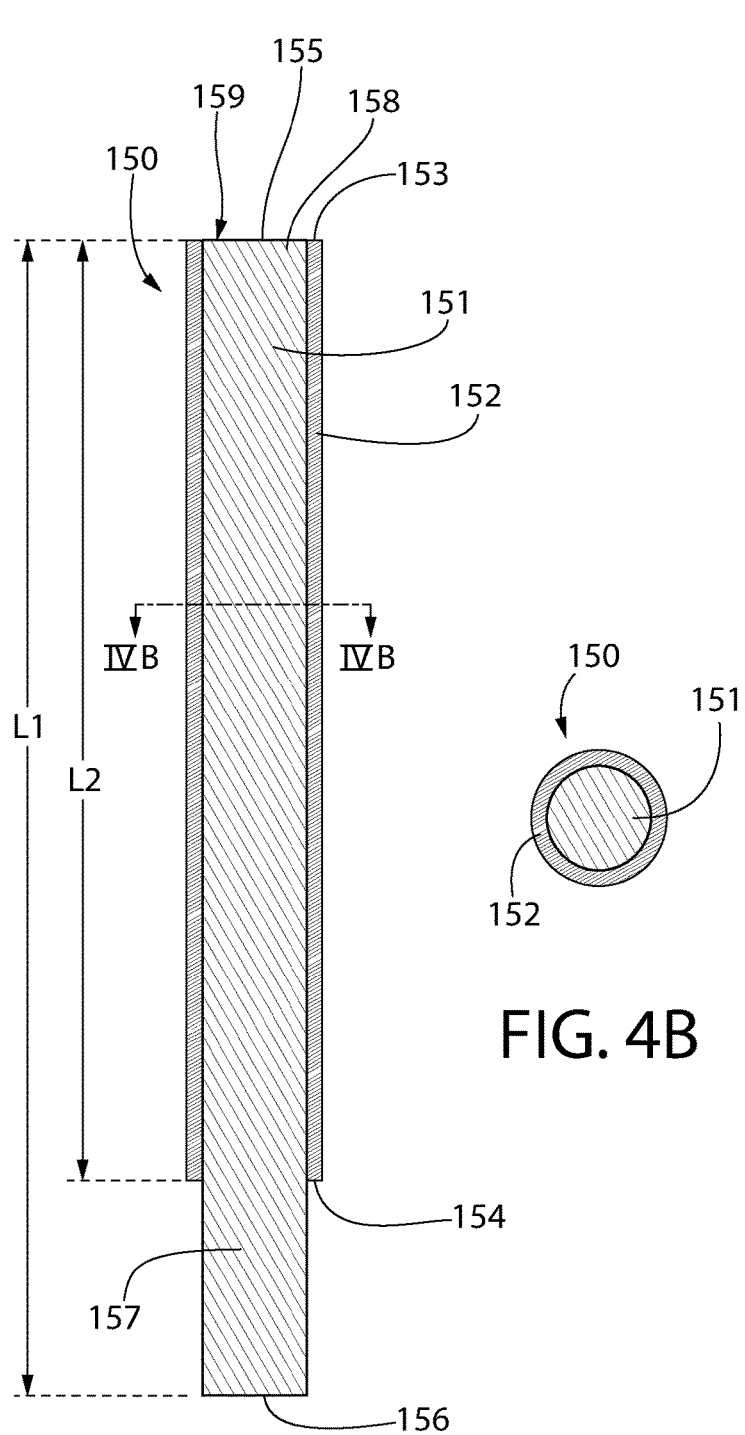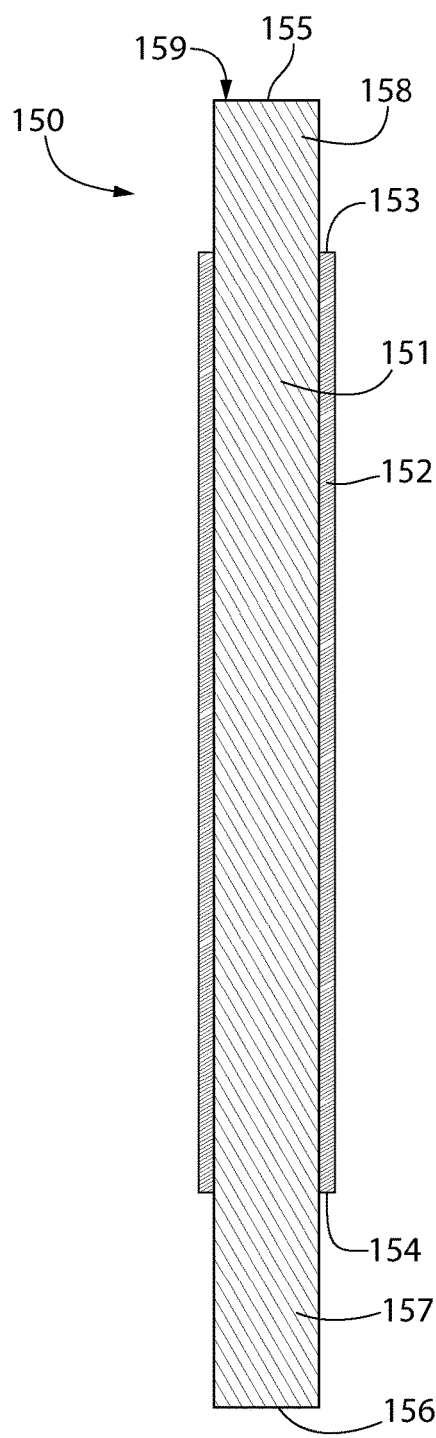
FIG. 4A
FIG. 4B
FIG. 4C

LIGHT-EMITTING ORAL CARE IMPLEMENT AND METHOD OF FORMING THE SAME

BACKGROUND

A toothbrush is used to clean the teeth by removing plaque and debris from the tooth surfaces. Toothbrushes have a handle for gripping and a head which is inserted into a user's mouth for tooth and oral surface cleaning. The head typically has bristles formed of nylon and sometimes also cleaning elements formed from elastomeric materials to perform the cleaning function. There is evidence that transmitting light onto the user's teeth may enhance the benefits of certain tooth cleaning agents that are used during toothbrushing. However, known toothbrushes that emit light are often bulky, uncomfortable to maneuver, and aesthetically displeasing. Thus, a need exists for a toothbrush or other oral care implement that emits light into the user's oral cavity while being aesthetically pleasing and comfortable to use.

BRIEF SUMMARY

The present invention may be directed, in one aspect, to an oral care implement that transmits light. The oral care implement may include a light delivery unit that includes a passageway through the head of the oral care implement and a tuft comprising a plurality of filaments located in the passageway, each of the filaments having a core component and a sheath component. The core component may have a transmittance that is greater than the transmittance of the sheath component. The core component may include a base portion that protrudes from a lower end of the sheath component such that the base portion forms an anchor portion of the tuft that anchors the tuft to the head of the oral care implement. Furthermore, the oral care implement may include a light source that transmits light through the anchor portion of the tuft and through the core components for transmittance from the filaments at a location above a front surface of the head.

In one embodiment, the invention can be a light-emitting oral care implement comprising: a body having a front surface; a light delivery unit comprising: a passageway in a portion of the body that terminates in an aperture in the front surface of the body; a tuft comprising a plurality of light-transmitting filaments, each of the light-transmitting filaments comprising: a core component formed of a first material having a first transmittance; a sheath component formed of a second material having a second transmittance, the sheath component surrounding the core component, the first transmittance being greater than the second transmittance; and the core component comprising a base portion that protrudes from a lower end of the sheath component; the tuft mounted within the passageway and comprising an anchor portion that anchors the tuft to the body, the base portions of the light-transmitting filaments forming the anchor portion; and a light source in operable cooperation with the anchor portion of the tuft such that light generated by the light source is transmitted through the anchor portion of the tuft, through the core components of the light-transmitting filaments of the tuft, and emitted from the light-transmitting filaments of the tuft at a location above the front surface of the body.

In another embodiment, the invention can be a light-emitting toothbrush comprising: a handle; a head having a front surface and a plurality of tuft holes; a plurality of bristle tufts mounted to the head within the plurality of tuft holes, the plurality of bristle tufts protruding from the front surface of the head to form a tooth cleaning element field; the plurality of bristle tufts comprising at least one light-transmitting tuft comprising a plurality of light-transmitting filaments, each of the light-transmitting filaments comprising: a core component formed of a first material having a first transmittance; a sheath component formed of a second material having a second transmittance, the sheath component surrounding the core component, the first transmittance being greater than the second transmittance; and the core component comprising a base portion that protrudes from a lower end of the sheath component; the at least one light-transmitting tuft comprising an anchor portion embedded in the head that is formed by the base portions of the light-transmitting filaments, the anchor portion formed of the first material; and a light source in operable cooperation with the anchor portion of the at least one light-transmitting tuft.

In a further embodiment, the invention can be a method of forming a light-emitting oral care implement, the method comprising: a) forming a plurality of filaments comprising: a core component formed of a first material having a first light transmittance; and a sheath component formed of a second material having a second light transmittance, the sheath component surrounding the core component, the first light transmittance being greater than the second light transmittance; b) for each of the filaments, removing a portion of the sheath component so that a base portion of the core component is exposed and protrudes from a lower end of a remaining portion of the sheath component, thereby forming a plurality of light-transmitting filaments; c) mounting the plurality of light-transmitting filaments to a body of the light-emitting oral care implement; and d) operably coupling a light source to the base portions of the plurality of light-transmitting filaments within the body.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 4A is a cross-sectional view of one of the light-transmitting filaments taken along line IVA-IVA of FIG. 3;

FIG. 4B is a cross-sectional view taken along line IVB-IVB of FIG. 4A;

FIG. 4C is a cross-sectional view taken along line IVA-IVA of FIG. 3 in accordance with an alternative embodiment of the present invention;

DETAILED DESCRIPTION

Figure 1:
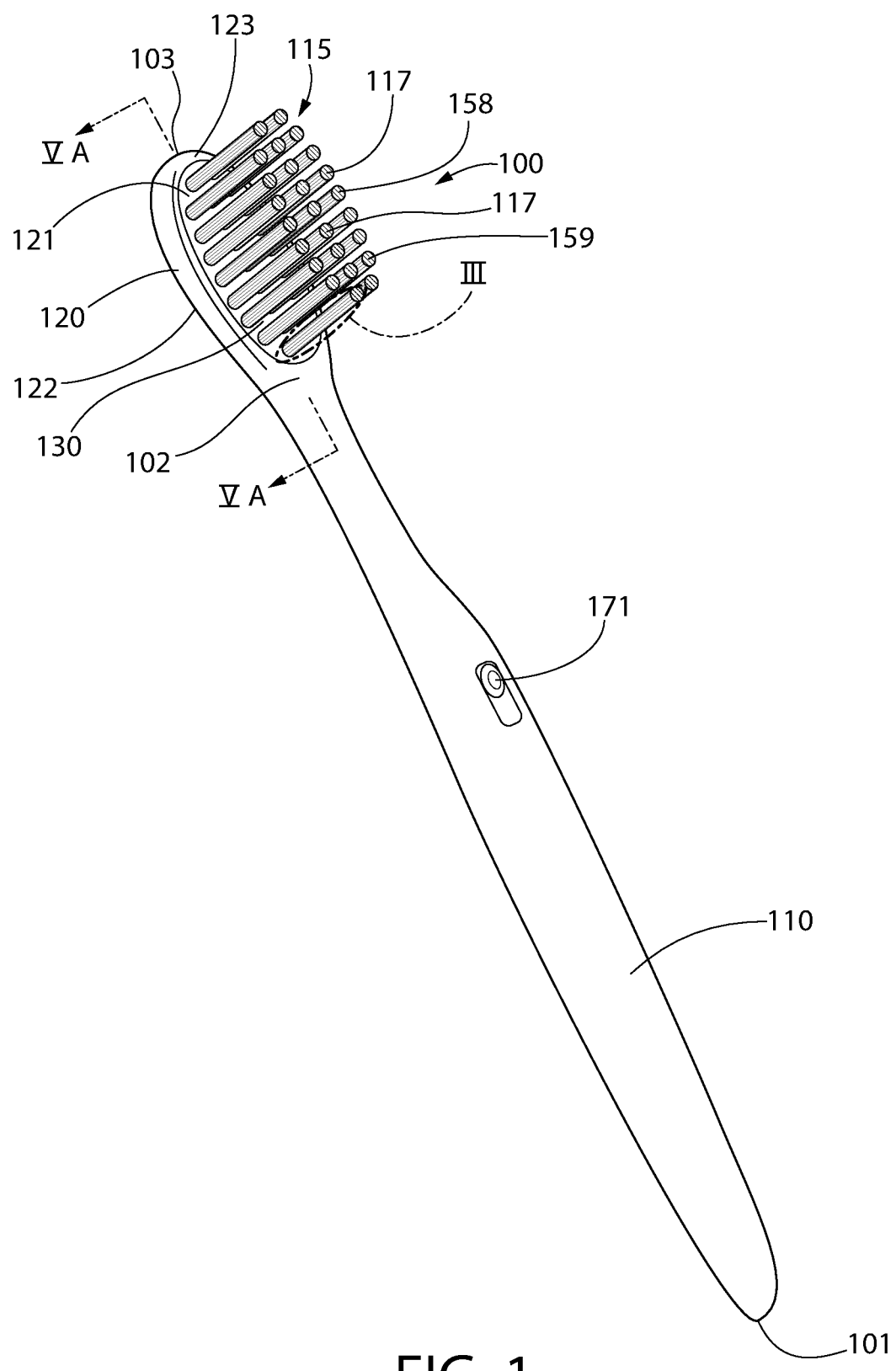
FIG. 1 is a front perspective view of an oral care implement in accordance with an embodiment of the present invention.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Referring first to FIG. 1, an oral care implement 100 is illustrated in accordance with one embodiment of the present invention. In the exemplified embodiment, the oral care implement 100 is in the form of a manual toothbrush. However, in certain other embodiments the oral care implement 100 can take on other forms such as being a powered toothbrush, a tongue scraper, a gum and soft tissue cleanser, a water pick, an interdental device, a tooth polisher, a specially designed ansate implement having tooth engaging elements, or any other type of implement that is commonly used for oral care. Furthermore, in still other embodiments the implement may not be limited to one that is used for oral care, and may be any type of personal care implement such as a manual or electric razor, a hairbrush, or the like. Thus, it is to be understood that the inventive concepts discussed herein can be applied to any type of oral or personal care implement unless a specific type of oral or personal care implement is specified in the claims.

In the exemplified embodiment, the oral care implement 100 comprises a handle 110 and a head 120. In certain embodiments the handle 110 and the head 120 are collectively referred to herein as a body of the oral care implement. The handle 110 extends from a proximal end 101 of the oral care implement 100 to a distal end 102 of the handle 110. Thus, in the exemplified embodiment the handle 110 includes the portion of the oral care implement 100 that is gripped during use and a neck of the oral care implement 100 that forms the transition region between the handle 110 and the head 120. The handle 110 is an elongated structure that provides the mechanism by which the user can hold and manipulate the oral care implement 100 during use. In the exemplified embodiment, the handle 110 is generically depicted having various contours for user comfort. Of course, the invention is not to be limited by the specific shape illustrated for the handle 110 in all embodiments and in certain other embodiments the handle 110 can take on a wide variety of shapes, contours, and configurations, none of which are limiting of the present invention unless so specified in the claims. The handle 110 may be formed of one or more rigid plastic materials such as for example without limitation polymers and copolymers of ethylene, propylene, butadiene, vinyl compounds, polyesters such as polyethylene terephthalate (PET), styrene-acrylonitrile (SAN), polyurethane, polyamide, cellulosic, acrylic, acrylonitrile butadiene styrene (ABS), or the like. A thermoplastic elastomer or other elastomeric material may be overmolded or otherwise adhered/affixed to the handle 110 to enhance the grip-ability of the handle 110 and prevent hand slippage during use.

The head 120 of the oral care implement 100 is coupled to the handle 110 and comprises a front surface 121 and an opposing rear surface 122. The head 120 extends from the distal end 102 of the handle 110 to a distal end 103 of the head 120. In the exemplified embodiment, a plurality of cleaning elements 115 are coupled to and extend from the head 120, and more specifically from the front surface 121 of the head 120. The cleaning elements 115 may be described herein as extending from a front surface of the body of the oral care implement 100.

Figure 2:
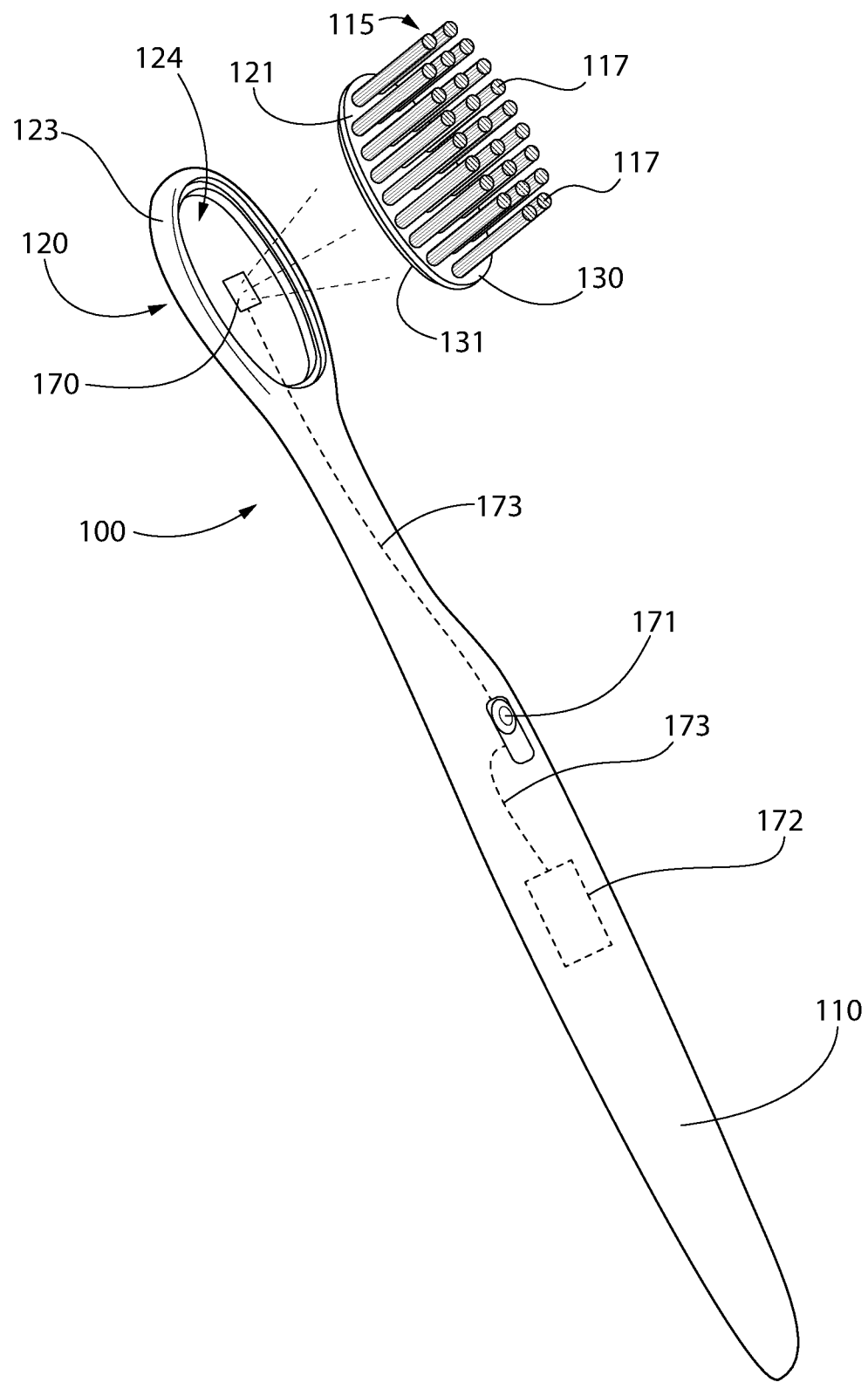
FIG. 2 is an exploded front perspective view of the oral care implement of FIG. 1.

The term "cleaning elements" is used herein in a generic sense to refer to any structure that can be used to clean, polish, or wipe the teeth and/or soft oral tissue (e.g. tongue, cheek, gums, etc.) through relative surface contact. Common examples of "cleaning elements" include, without limitation, bristle tufts, filament bristles, fiber bristles, nylon bristles, spiral bristles, tapered bristles, rubber bristles, elastomeric lamella, elastomeric protrusions, flexible polymer protrusions, combinations thereof and/or structures containing such materials or combinations. The cleaning elements may include tapered bristles, non-tapered (i.e., end rounded) bristles, and combinations thereof. Any combination of the various types of tooth cleaning elements may be used on the oral care implement 100 in different embodiments. Some specific arrangements of the cleaning elements 115 are described herein as forming a part of an exemplary embodiment of the oral care implement 100. As discussed in detail below, in certain embodiments the cleaning elements may be light-transmitting filaments that are arranged together in a tuft that is coupled to the head 120. In FIGS. 1 and 2 the cleaning elements are generically depicted. However, the details of the cleaning elements, particularly as light-transmitting filaments, are illustrated in FIGS. 3-4C, 5C, 6, and 7B.

As noted above, in the exemplified embodiment the cleaning elements are light-transmitting filaments that are arranged in bundles or tufts that extend together from a single tuft hole formed into the head 120 (or head plate). These light-transmitting filaments may be tapered or non-tapered. In certain embodiments the cleaning elements may include the light-transmitting filaments described in detail below and other types of cleaning elements such as those described herein above. In embodiments that use elastomeric elements as one or more of the cleaning elements 115, suitable elastomeric materials may include any biocompatible resilient material suitable for uses in an oral hygiene apparatus. To provide optimum comfort as well as cleaning benefits, the elastomeric material of any such tooth or soft tissue engaging elements may have a hardness property in the range of A8 to A25 Shore hardness. One suitable elastomeric material is styrene-ethylene/butylene-styrene block copolymer (SEBS) manufactured by GLS Corporation. Nevertheless, SEBS material from other manufacturers or other materials within and outside the noted hardness range could be used. The cleaning elements 115 may be coupled to the head 120 using any technique known in the art, such as stapling, anchor free tufting, in-mold tufting, AMR, or the like, the details of which will be described in more detail below. The invention is not to be limited by the manner in which the cleaning elements 115 are coupled to the head 120 in all embodiments.

As discussed above, in the exemplified embodiment the plurality of cleaning elements 115 extend from the front surface 121 of the head 120. A tongue or soft tissue cleaner (not illustrated) may be positioned on the rear surface 122 of the head 120. In the exemplified embodiment, the head 120, or at least a portion thereof, is formed integrally with the handle 110 as a single unitary structure using a molding, milling, machining, or other suitable process. However, in other embodiments the handle 110 and the head 120 may be formed as separate components which are operably connected at a later stage of the manufacturing process by any suitable technique known in the art, including without limitation thermal or ultrasonic welding, a tight-fit assembly, a coupling sleeve, threaded engagement, adhesion, or fasteners. Thus the handle 110 and the head 120 may, in certain embodiments, be formed of any of the rigid plastic materials described above, although the invention is not to be so limited in all embodiments and other materials that are commonly used during toothbrush manufacture may also be used.

Figure 5A:
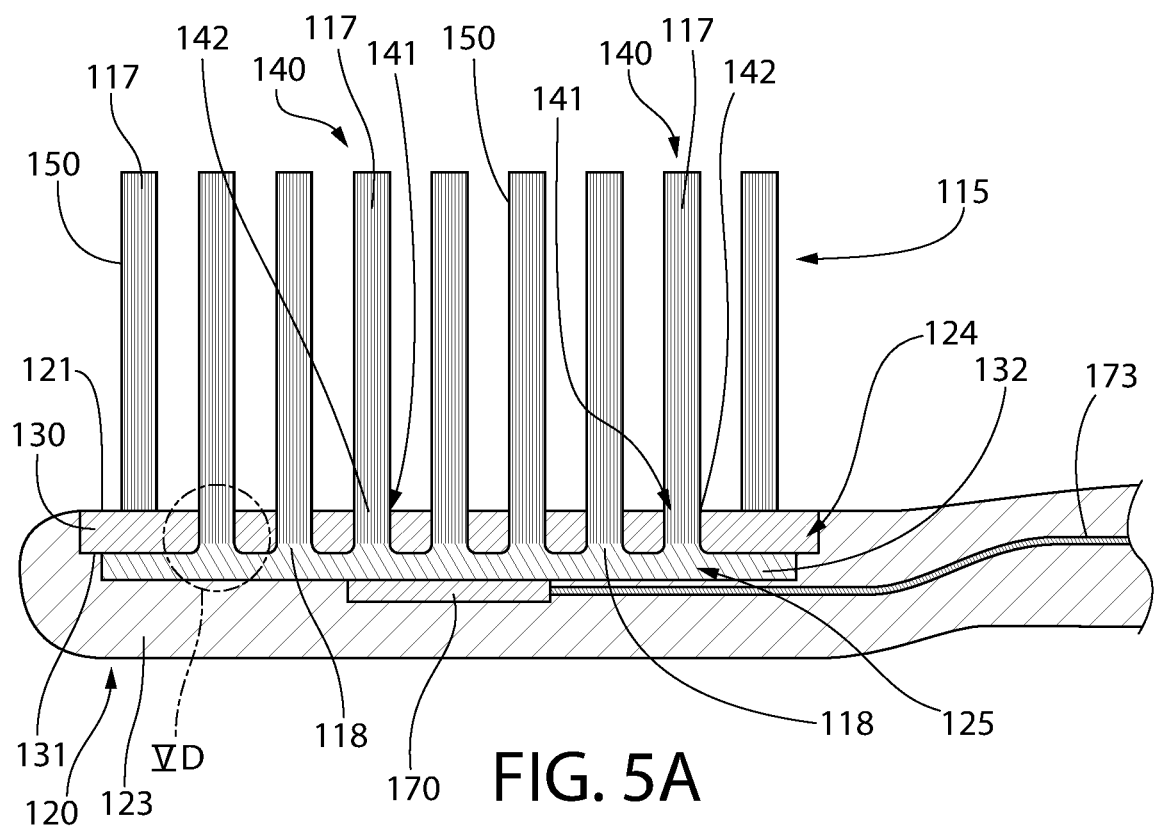
FIG. 5A is a cross-sectional view taken along line VA-VA of FIG. 1.

Referring to FIGS. 1, 2, and 5A concurrently, the oral care implement 100 will be further described. In the exemplified embodiment, the oral care implement 100 comprises a light delivery unit 140 that comprises a passageway 141 in a portion of the head 120 that terminates in an aperture 142 in the front surface 121 of the head 120. Of course, although the passageway 141 and aperture 142 are exemplified in the head 120, they can be formed in any other part of the body in other embodiments, such as parts of the handle 110 or the like. The light delivery unit 140 also comprises a tuft 117 comprising a plurality of light-transmitting filaments 150 (see FIGS. 3-4C and 6 described below). The tufts 117 are mounted within the passageways 141 as described directly below.

In the exemplified embodiment, the head 120 of the oral care implement 100 comprises a support 123 that is formed integrally with the handle 120 and a plate 130 that is formed separately from the handle 120 and is operably coupled to the support 123 during the manufacturing process as discussed herein below. An upper surface of the plate 130 forms the front surface 121 of the head 120 and the plate 130 comprises a rear surface 131 opposite the front surface 121. The support 123 of the head 120 comprises a basin 124 into which the plate 130 is positioned to form the oral care implement 100.

Specifically, during manufacturing (which will be discussed in more detail below with reference to FIGS. 9A-9E) the tufts 117 are coupled to the plate 130 by inserting the tufts 117 through holes in the plate 130 that extend from the front surface 121 to the rear surface 131. In the exemplified embodiment, the holes in the plate 130 are the passageways 141 noted above. The light-transmitting filaments 150 that form the tuft 117 are inserted through the plate 130 so that bottom portions of each of the light-transmitting filaments 150 protrude from the rear surface 131 of the plate 130. The bottom portions of the light-transmitting filaments 150 of the tuft 117 are then melted together to form an anchor portion 118 of the tuft 117 that anchors the tuft 118 to the head 120 or body.

Furthermore, where more than one tuft 117 is coupled to the head 120 or body, the anchor portions 118 of all of the tufts 117 are melted or fused together to form a melt matte or simply a matte 132. After melting, the matte 132 hardens to form a layer of the cleaning element material that is adjacent to the rear surface 131 of the plate 130. Whereas the anchor portion 118 of each tuft 117 anchors that particular tuft 117 to the head 120, the matte 132 couples the collection of all of the tufts 117 to the plate 130 and prevents the tufts 117 from being pulled through the holes in the plate 130 (i.e., the passageways 141). After melting the anchor portions 118 of the tufts 117 to form the matte 132, the plate 130 is inserted into the basin 124 of the support 123 and the plate 130 is affixed to the support 123 using techniques known in the art such as ultrasonic welding, adhesion, fasteners, or the like. With the plate 130 coupled to the support 123, an internal cavity 125 is formed between the plate 130 and the support 123 such that the matte 132 is disposed within the internal cavity 125.

Furthermore, the oral care implement 100 comprises a light source 170 that is in operable cooperation with the anchor portions 118 of the tufts 117. The light source 170 may be capable of alternating between an on state in which the light source 170 generates and transmits light and an off state in which the light source 170 is powered off and no light is being generated and transmitted. As a result of the positioning of the light source 170 in operable cooperation with the anchor portions 118 of the tufts 117, light generated by the light source 170 is transmitted through the anchor portion 118 of the tuft 117 and is emitted from the light-transmitting filaments 150 (see FIGS. 3-4C) of the tuft 170 at a location above the front surface 121 of the head 120. Specifically, in certain embodiments the light is emitted from distal ends of the tuft 117 which are spaced from the front surface 121 of the head 120. In the exemplified embodiment, the light source 170 is disposed within the internal cavity 124 that is formed between the plate 130 and the support 123 of the head 120. Of course, the light source 170 may be positioned at other locations, an example of which will be described below with reference to FIG. 5B.

In the exemplified embodiment, the light source 170 is operably coupled to a switch 171 and a power source 172 via wires 173 or other types of electrical conductors. In the exemplified embodiment the switch 171 is a slide switch but it may be a button switch, multiple buttons, a toggle, a joystick, a selector switch, a conductive switch, a proximity switch, a temperature switch, a rotary switch, or any other type of switch as desired to alternate the light source 170 between the on and off states. In the exemplified embodiment the switch 171 is positioned between the power source 172 and the light source 170 to permit and prevent electrical power of the power source 172 from powering the light source 170 as desired. However, the switch 171 may be positioned at other locations relative to the power source 172 and the light source 170 in other embodiments. In the exemplified embodiment the power source 172 is positioned within the handle 110 but it may be positioned within the head 120 or neck in other embodiments. Furthermore, in the exemplified embodiment the power source 172 is one or more batteries. In other embodiments the power source 172 may be a plug that plugs into an electrical socket.

The light source 170 may be any type of light source desired to achieve a particular purpose. For example, the light source may transmit ultraviolet light, blue light, white light, or the like to facilitate and enhance the anti-bacterial and/or tooth whitening effects of an agent being applied to a user's mouth and particularly teeth during oral hygiene activities. The light source 170 may include incandescent light, LEDs, halogen light, or any other type of light desired.

Figure 3:
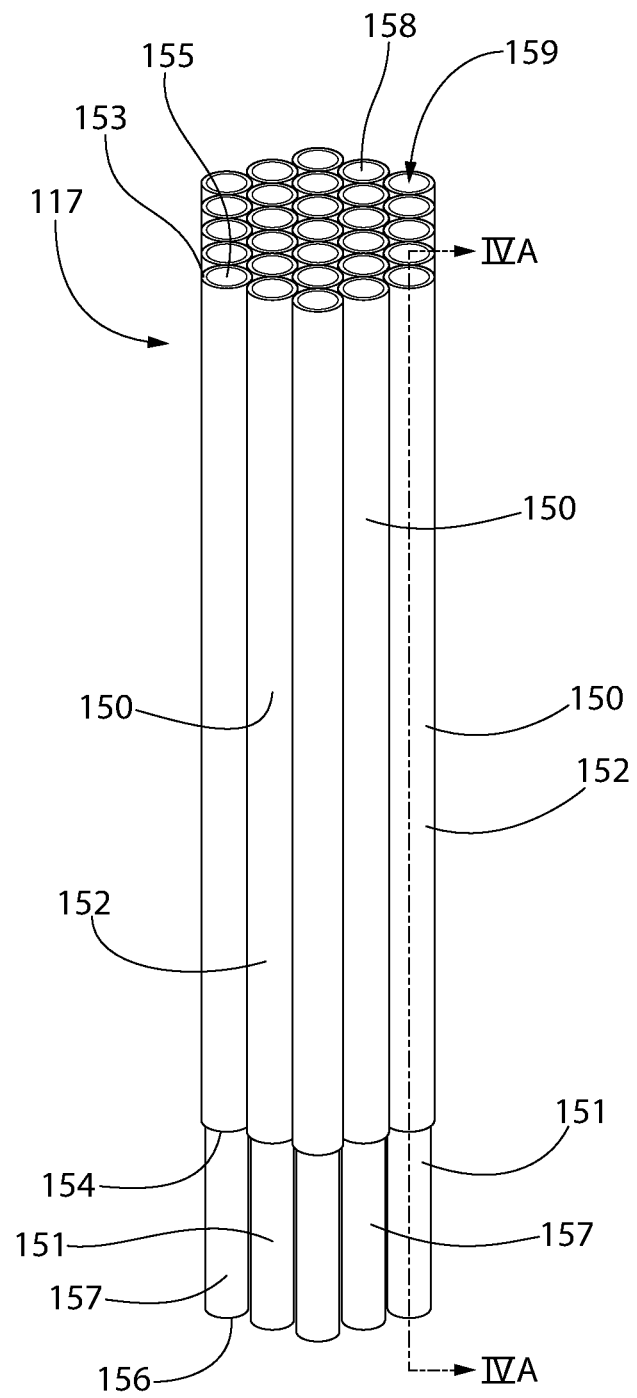
FIG. 3 is a close-up view of area III of FIG. 1 depicting a tuft comprising a plurality of light-transmitting filaments.

Referring now to FIGS. 3-4B, the details of one of the tufts 117 and the light-transmitting filaments 150 that form the tuft 117 will be described. As noted above, in the exemplified embodiment each of the tufts 117 comprises a plurality of the light-transmitting filaments 150. In certain embodiments at least one of the tufts 117, and in some cases all of the tufts 117, may consist of only light-transmitting filaments 150. However, the invention is not to be so limited and one or more of the tufts 117 may include some light-transmitting filaments 150 and some other types of cleaning elements (i.e., elastomeric cleaning elements or lamella and filaments that are non-light transmitting). Furthermore, some of the tufts 117 may include light-transmitting filaments 150 and others of the tufts 117 may not include light-transmitting filaments 150. Specifically, the oral care implement 100 may include a plurality of bristle tufts mounted to the head 120 to form a tooth cleaning element field. The plurality of bristle tufts may comprise at least one light-transmitting tuft such as one of the tufts 117 described herein. Thus, various permutations are possible within the scope of this application. However, in the exemplified embodiment there is at least one tuft 117 that comprises (or in some instances consists of) a plurality of the light-transmitting filaments 150.

The light-transmitting filaments 150 comprise a core component 151 formed of a first material having a first transmittance and a sheath component 152 formed of a second material having a second transmittance. The sheath component 152 circumferentially surrounds the core component 151 along at least a portion of the length of the core component 151. As used herein, transmittance is the effectiveness of a material in transmitting light or allowing light to pass through the material and it may also be referred to herein as the light refractive index of the material. In the exemplified embodiment, the first transmittance of the first material is greater than the second transmittance of the second material. Thus, light is better able to transmit through the core component 151 than through the sheath component 152. In certain embodiments the second material of the sheath component 152 is opaque and the first material of the core component 151 is translucent or transparent. In such embodiments, the sheath component 152 may substantially prevent light from passing therethrough to prevent light dispersion and ensure that all light from the light source 170 transmits through the core component 151. Of course, the invention is not to be so limited in all embodiments and the sheath component 152 need not be opaque in all embodiments.

In the exemplified embodiment, the sheath component 152 extends from an upper end 153 to a lower end 154 and the core component 151 extends from an upper end 155 to a lower end 156. Furthermore, in the exemplified embodiment the upper ends 153, 155 of the core and sheath components 151, 152 are located on the same plane and collectively form a distal end 159 of the light-transmitting filament 150. Thus, in the exemplified embodiment the core and sheath components 151, 152 extend the same distance from the front surface 121 of the head 120 when the light-transmitting filaments 150 are coupled to the head 120. However, in other embodiments, such as the embodiment of FIG. 4C, the core component 151 may protrude from or extend further than the upper end 153 of the sheath component 152. In this embodiment, the core component 151 forms the entirety of the distal end 159 of the light-transmitting filament 150. In certain non-exemplified embodiments, the light-transmitting filament 150 may be tapered. This may include both the core and sheath components 151, 152 tapering towards the distal end 159 of the light-transmitting filament 150 or, as in the embodiment of FIG. 4C, just the portion of the core component 151 that protrudes from the upper end 153 of the sheath component 152 tapering towards the distal end 159 of the light-transmitting filament 150.

In both the embodiment of FIG. 4A and the embodiment of FIG. 4C, the core component 151 has a light-emitting portion 158 that is exposed at the distal end 159 of the light-transmitting filament 150. The difference between the two embodiments is that in FIG. 4A the core component 151 (and the light-emitting portion 158 thereof) does not protrude beyond the upper end 153 of the sheath component 152 and in FIG. 4B the core component 151 does protrude beyond the upper end 153 of the sheath component 152 such that the light emitting portion 158 is located beyond the upper end 153 of the sheath component 152. In both embodiments, the core component 151 comprises a base portion 157 that protrudes from the lower end 154 of the sheath component 152. Thus, the core component 151 has a length $L_1$ measured from the lower end 156 of the core component 151 to the upper end 155 of the core component 151 that is greater than a length $L_2$ of the sheath component 152 measured form the lower end 154 of the sheath component 152 to the upper end 153 of the sheath component 152. The base portion 157 of the core component 151 that protrudes from the lower end 154 of the sheath component 152 may have a length that is approximately between one-third and one-tenth of the length $L_1$ of the core component 151 in some embodiments, although the invention is not to be so limited in all embodiments.

Figure 5B:
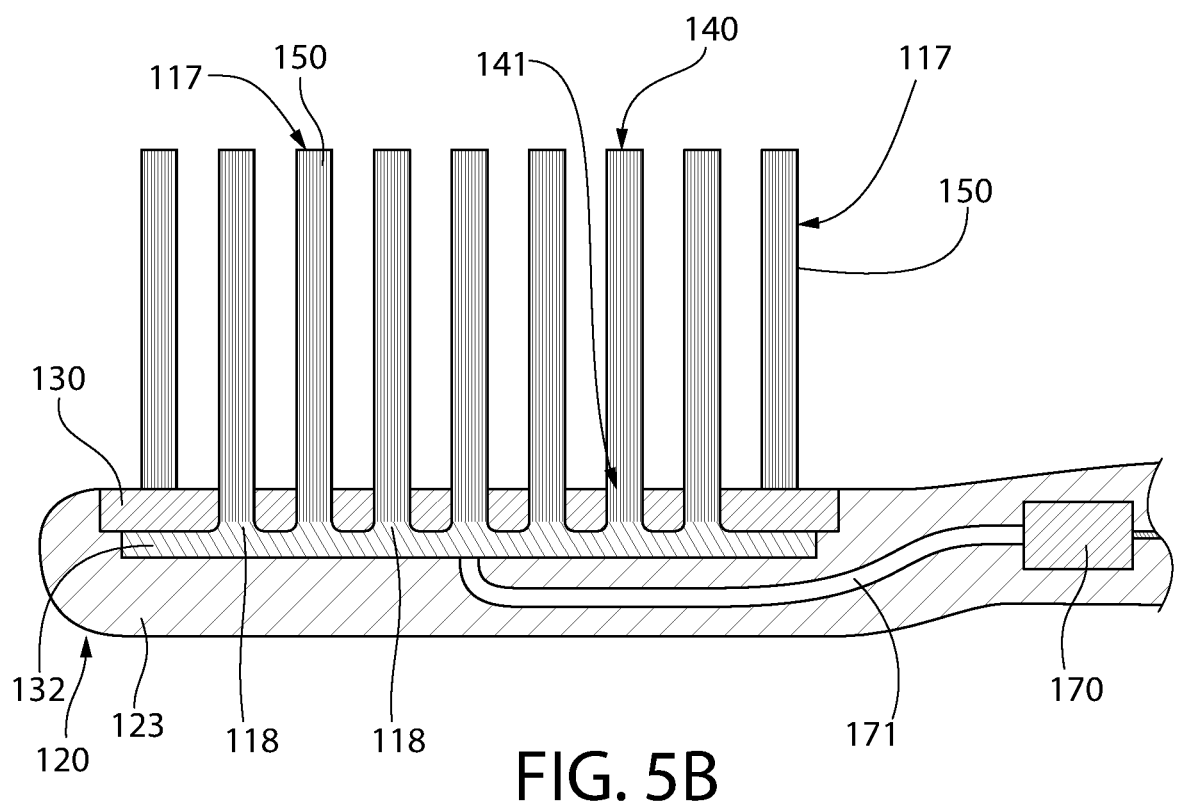
FIG. 5B is a cross-sectional view taken along line VA-VA of FIG. 1 in accordance with an alternative embodiment of the present invention.
Figure 5C:
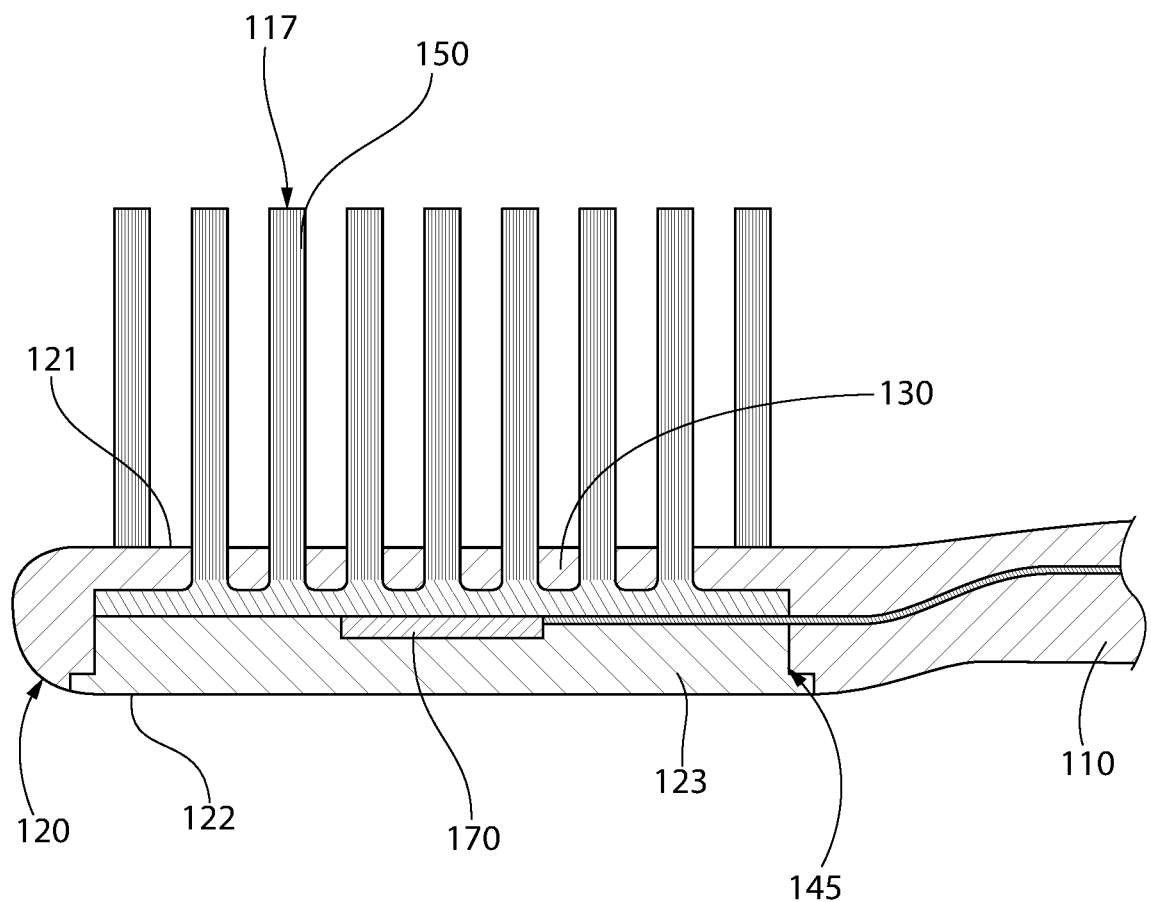
FIG. 5C is a cross-sectional view taken along line VA-VA of FIG. 1 in accordance with another alternative embodiment of the present invention.
Figure 5D:
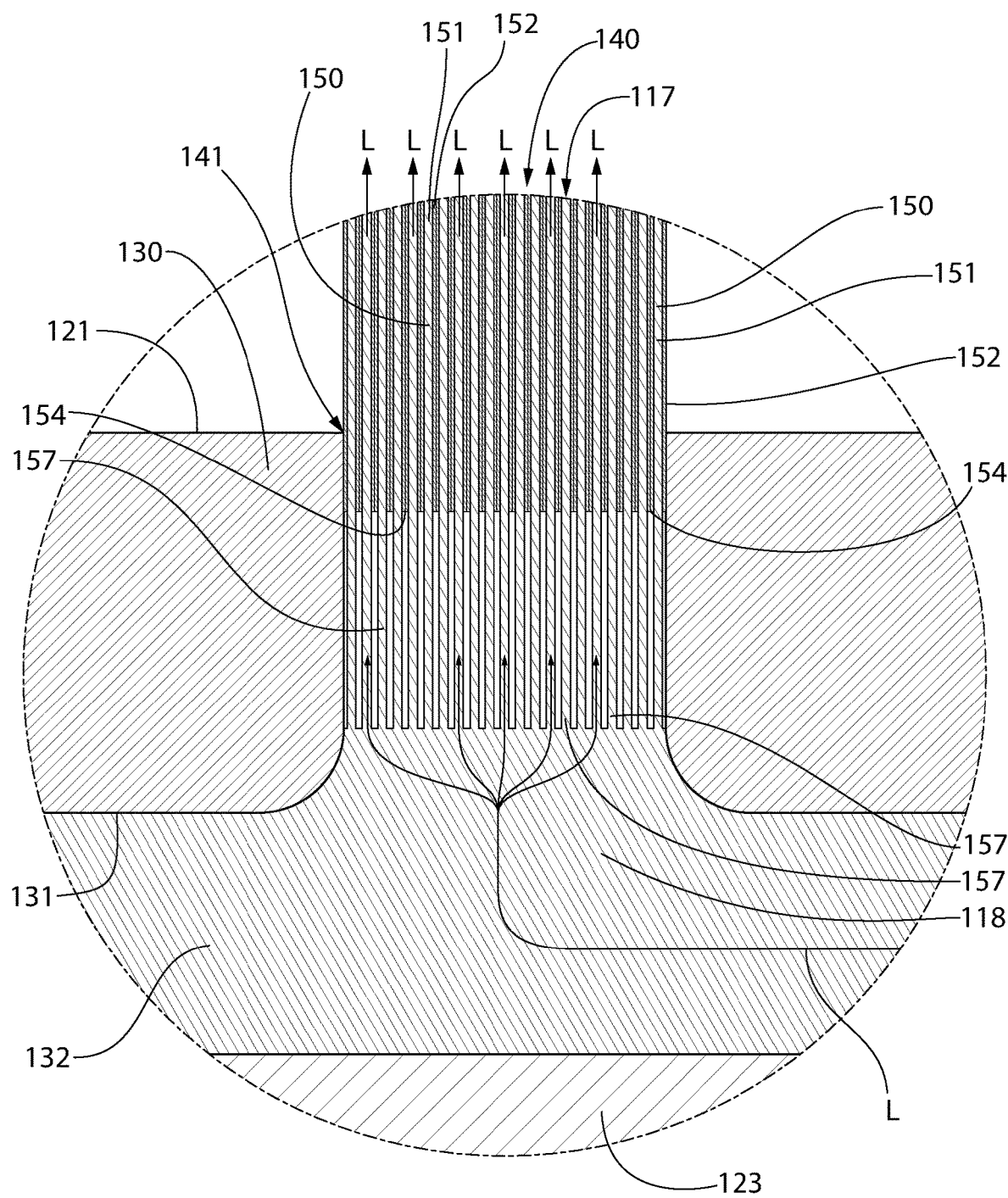
FIG. 5D is a close-up view of area VC of FIG. 5A.

Referring now to FIGS. 5A and 5D concurrently, the oral care implement will be further described. As discussed above, the light delivery unit 140 comprises the passageway 141 and at least one of the tufts 117 comprising a plurality of the light-transmitting filaments 150 mounted within the passageway 141 so that the anchor portion 118 of the tuft 117 anchors the tuft 117 to the body or head 120 of the oral care implement 100. As can be seen in FIG. 5D, in the exemplified embodiment the base portions 157 of the core component 151 of the light-transmitting filaments 150 form the anchor portion 118 of the tuft 117. Specifically, because the base portions 157 of the core components 151 protrude from/beyond the lower ends 154 of the sheath components 152, it is the base portions 157 of the core components 151 alone, which are formed of the first material, that form the anchor portion 118 of the tuft 117 and that facilitate anchoring the tufts 117 within the passageways 141. Specifically, the anchor portion 118 of each tuft 117 is formed by fusing the base portions 157 of the core components 151 of the light-transmitting filaments 150 within the tuft 117 together such that the anchor portion 118 of each tuft 117 is a monolithic mass of the first material that is free of the second material.

Furthermore, in certain embodiments the oral care implement 100 may include a plurality of the light delivery units 140. Thus, the head 120 (or body) includes a plurality of the passageways 141, and one of the tufts 117 comprising the light-transmitting filaments 150 is disposed within each of the passageways 141. In such an embodiment, the anchor portions 118 of each tuft 117 that is coupled to the head 120 are fused together to form the matte 132. Thus, the matte 132 is also formed only of the first material and is free of the second material. Specifically, because the anchor portion 118 of each tuft 117 is formed solely of the first material and because the matte 132 is formed by fusing the anchor portions 118 of the various tufts 117 together, the matte 132 formed by many of the anchor portions 118 is also a monolithic mass of the first material.

Ensuring that the second material is not forming any part of the matte 132 or the anchor portions 118 of the tufts 117 facilitates the transmission of light from the light source 170 through the light-transmitting filaments 150 as discussed below. If the second material, which has a lower transmittance than the first material (and which may be opaque) formed a part of the matte 132 and/or the anchor portions 118 of the tufts 117, the light transmitted from the light source 170 may be partially or fully blocked from passing through and being emitted by the light-transmitting filaments 150 at a distance that is spaced from the front surface 121 of the head 120 or body.

As noted above, the light source 170 is positioned so as to be in operable cooperation with the anchor portion 118 of each tuft 117 so that the light generated by the light source 170 is transmitted through the anchor portion 118 of the tuft 117 and through the core components 151 of the light-transmitting filaments 150 of the tuft 117. The light generated by the light source 170 is then emitted from the light-transmitting filaments 150 of the tuft 117 at a location above the front surface 121 of the head 120. More specifically, because the first material of the core component 151, which has a greater light transmittance than the second material of the sheath component 152, forms the entirety of the anchor portions 118 of the tufts 117, the light is able to be transmitted through the anchor portions 118 of the tufts 117 and through the core components 151 of the light-transmitting filaments 150 to be finally emitted from the distal end 159 of the light-transmitting filament 150 or from the light-emitting portion 158 of the core components 151. The light does not typically transmit through the sheath component 152 (or does so in a much smaller amount than through the core component 151) due to its lower light transmittance as compared to the core component 151. As a result, the sheath component 152 prevents or minimizes light dispersion and permits the light to pass through the center of the light-transmitting filament 150 within the core component 151 and to become visible at the exposed light-emitting portion 158 of the core component 151. The transmission of light from the light source 170 is depicted with lines and arrows labeled "L" in FIG. 5D.

Furthermore, where there are a plurality of the light delivery units 140, the light source 170 is in operable cooperation with the matte 132 such that light generated by the light source 170 is transmitted through the matte 132 and through the core component 151 of the light-transmitting filaments 150 of each tuft 117 of each of the light delivery units 170. The light generated by the light source 170 is then emitted from the light-transmitting filaments 150 of each tuft 117 of each of the light delivery units 140 at a location above the front surface 121 of the head 120 or body. In certain embodiments, due to the lower transmittance of the second material of the sheath component 152, the light is not visible or is barely visible as it passes through the light-transmitting filaments 150. Rather, in certain embodiments the light may only be visible at the exposed light-emitting portions 158 of the core component 151 of the light-transmitting filaments 150 that form the distal ends 159 of the light-transmitting filaments 150 and are therefore spaced apart from the front surface 121 of the head 120. In the exemplified embodiment, the light source 170 is positioned directly adjacent to the matte 132.

In certain embodiments, due to the sheath component 152 at least partially blocking the light from being seen or emitted as the light rays travel through the light-transmitting filaments 150, a desirable aesthetic effect may be achieved along with a hygienic effect. Specifically, if the sheath component 152 of each light-transmitting filament is opaque or very resistant to the transmission of light, the light will only become visible at the distal end 159 of each light-transmitting filament 150 as the core component 151 becomes exposed at the light-emitting portion 158. Even if the sheath component 152 permits some light to pass through it, a much greater amount of light will be directed through the core component 151 and become visible to a user only at the distal end 159 of the light-transmitting filament 150. This will create a desirable aesthetic and may also precisely direct the light into desired areas of the mouth through the core component 151 of the light-transmitting filaments 150.

The light-transmitting filaments 150 may operate in a similar manner to an optical fiber such that light is transmitted between the two ends of the light-transmitting filaments 150 with the core component 151 due to the core component 151 being surrounded by the sheath component 152 which has a lower index of refraction or transmittance than the core component 151. In some embodiments, the light may remain in the core component 151 by the phenomenon of total internal reflection.

Referring briefly to FIG. 5B, a slightly modified version of the oral care implement 100 is illustrated. In this embodiment, the components and features of the oral care implement 100 are identical to that which has been described herein except that the light source 170 is no longer positioned within the internal cavity 125 and adjacent to the anchor portions 118 of the tufts 117 and/or the matte 132. Rather, in this embodiment the light source 170 is positioned in the neck or handle 110 of the oral care implement 100 and a light pipe 171 directs the light generated by the light source 170 to the matte 132 so that the light is emitted through the light-transmitting filaments 150 in the same manner as described herein above. Specifically, the light pipe 171 extends from the light source 170 to the anchor portions 118 of the tufts 117 and/or the matte 132 to direct the light form the light source 170 to the anchor portions 118 of the tufts 117 and/or the matte 132. The light pipe 171 may be a hollow region of the oral care implement 100 or it may be a structure that is known to facilitate the transfer of light such as any of the various known types of light tubes.

Referring briefly to FIG. 5C, another slightly modified version of the oral care implement 100 is illustrated. In the embodiment discussed above, the support 123 of the head 120 and the handle 110 are integrally formed and the plate 130 is separately formed from the support 123 and the handle 110 and later coupled thereto. In FIG. 5C, the plate 130 is integrally formed with the handle 110 and the support 123 is separately formed from the handle 110 and the plate 130. Specifically, in this embodiment after the tufts 117 are coupled to the plate 130 and melted/fused as described herein above, the support 123 is formed to secure the tufts 117 to the plate 130 and prevent the tufts 117 from being removed via the rear surface 122 of the head 120. In this embodiment the support 123 may be formed via an injection molding process using a rigid plastic material similar to the material used to form the plate 130 and the handle 110. Alternatively, the support 123 may be formed via an injection molding process out of a resilient or elastomeric material, such as a thermoplastic elastomer. The support 123 may be injection molded directly into a basin or recess 145 that is formed into the rear surface 122 of the head 120 or it may be formed separately from the plate 130 and handle 110 and later affixed thereto using adhesive, ultrasonic welding, or the like. In certain embodiments, the support 123 may also include protrusions or nubs/ridges extending from its exposed surface such that the support 123 may function as a tongue or soft tissue cleanser. The exposed surface of the support 123 may form the entirety or a portion of the rear surface 122 of the head 120.

Figure 6:
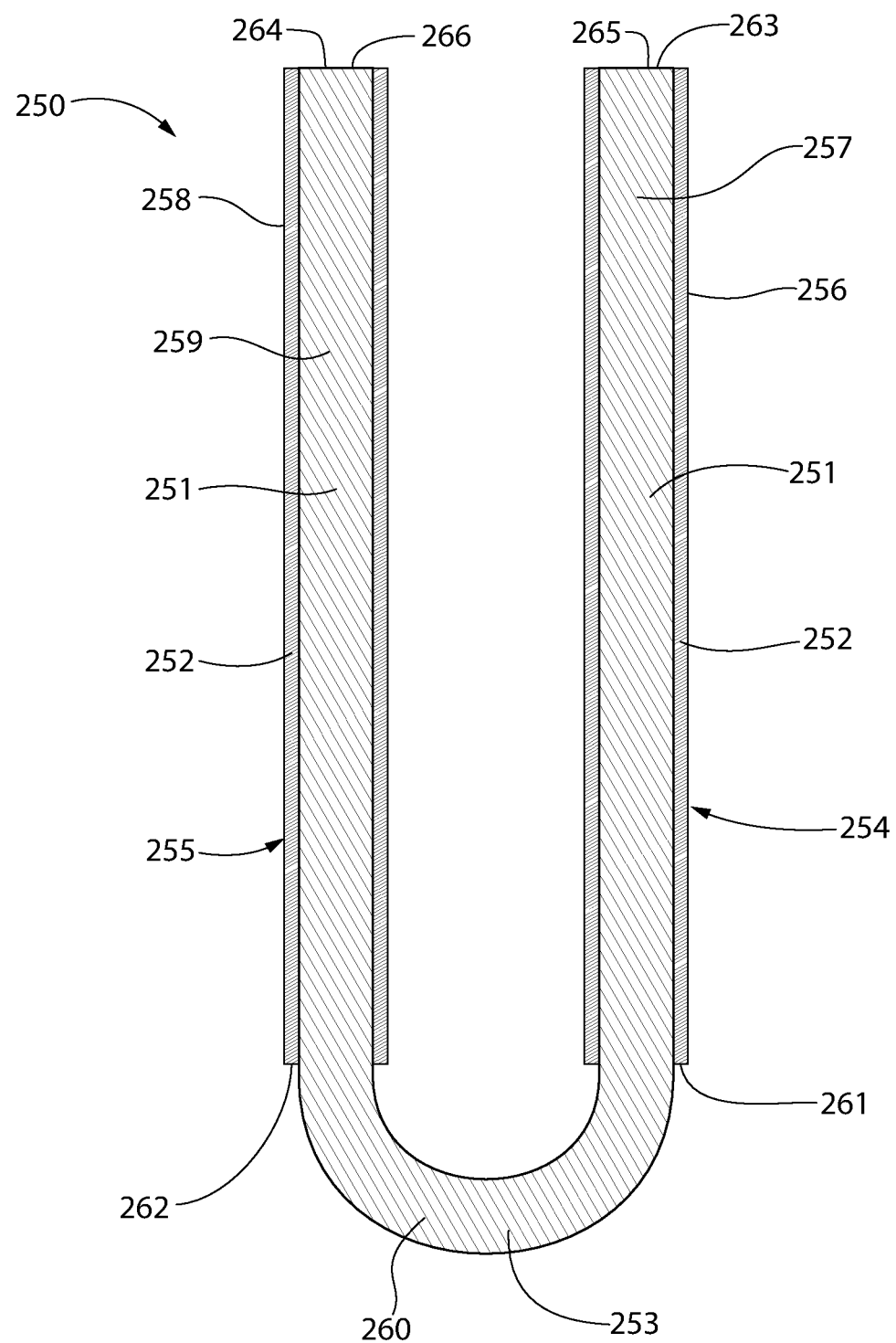
FIG. 6 is a cross-sectional view depicting a single one of the light-transmitting filaments of the oral care implement of FIG. 1 in accordance with an alternative embodiment of the present invention.

Referring now to FIG. 6, an alternative light-transmitting filament 250 is illustrated in accordance with an embodiment of the present invention. The light-transmitting filament 250 may be used in place of the light-transmitting filament 150 discussed above. While the light-transmitting filament 150 discussed above is generally best suited for use when the light-transmitting filament 150 is coupled to the head using an anchor-free tufting technique, the light-transmitting filament 250 is best suited for use when the light-transmitting filament 250 is coupled to the head using staple technology.

The light-transmitting filament 250 is a U-shaped filament comprising a core component 251 and a sheath component 252. The sheath component 252 surrounds the core component 251 along a portion of the length of the core component 251. More specifically, the light-transmitting filament 250 comprises a bight portion 253, a first leg portion 254 extending from a first end of the bight portion 253, and a second leg portion 255 extending from a second end of the bight portion 253 that is opposite the first end. The first leg portion 254 comprises a first section 256 of the sheath component 252 and a first section 257 of the core component 251, the first section 256 of the sheath component 252 surrounding the first section 257 of the core component 251. The first leg portion 254 terminates at a distal end 263. The first section 256 of the sheath component 252 terminates in a lower end 261. The second leg portion 255 comprises a second section 258 of the sheath component 252 and a second section 259 of the core component 251, the second section 258 of the sheath component 252 surrounding the second section 259 of the core component 251. The second leg portion 255 terminates at a distal end 264. The second section 258 of the sheath component 252 terminates in a lower end 262. The bight portion 253 comprises a third section 260 of the core component 251. The third section 260 of the core component 251 protrudes from and extends between the lower ends 261, 262 of the first and second sections 256, 258 of the sheath component 252. The bight portion 253 is free of the sheath component 252 such that the bight portion 253 is formed entirely from the core component 251.

Furthermore, first section 257 of the core component 251 comprises a light-emitting portion 265 that is exposed at the distal end 263 of the first leg 254 of the light-transmitting filament 250. The second section 259 of the core component 251 comprises a light-emitting portion 266 that is exposed at the distal end 264 of the second leg 255 of the light-transmitting filament 250. In the exemplified embodiment the light-emitting portions 265, 266 do not protrude from the upper ends of the first and second sections 256, 258 of the sheath component 252. However, in alternative embodiments the light-emitting portions 265, 266 may protrude from the upper ends of the first and second sections 256, 258 of the sheath component 252 similar to that which was described above with reference to FIG. 4C.

Figure 7A:
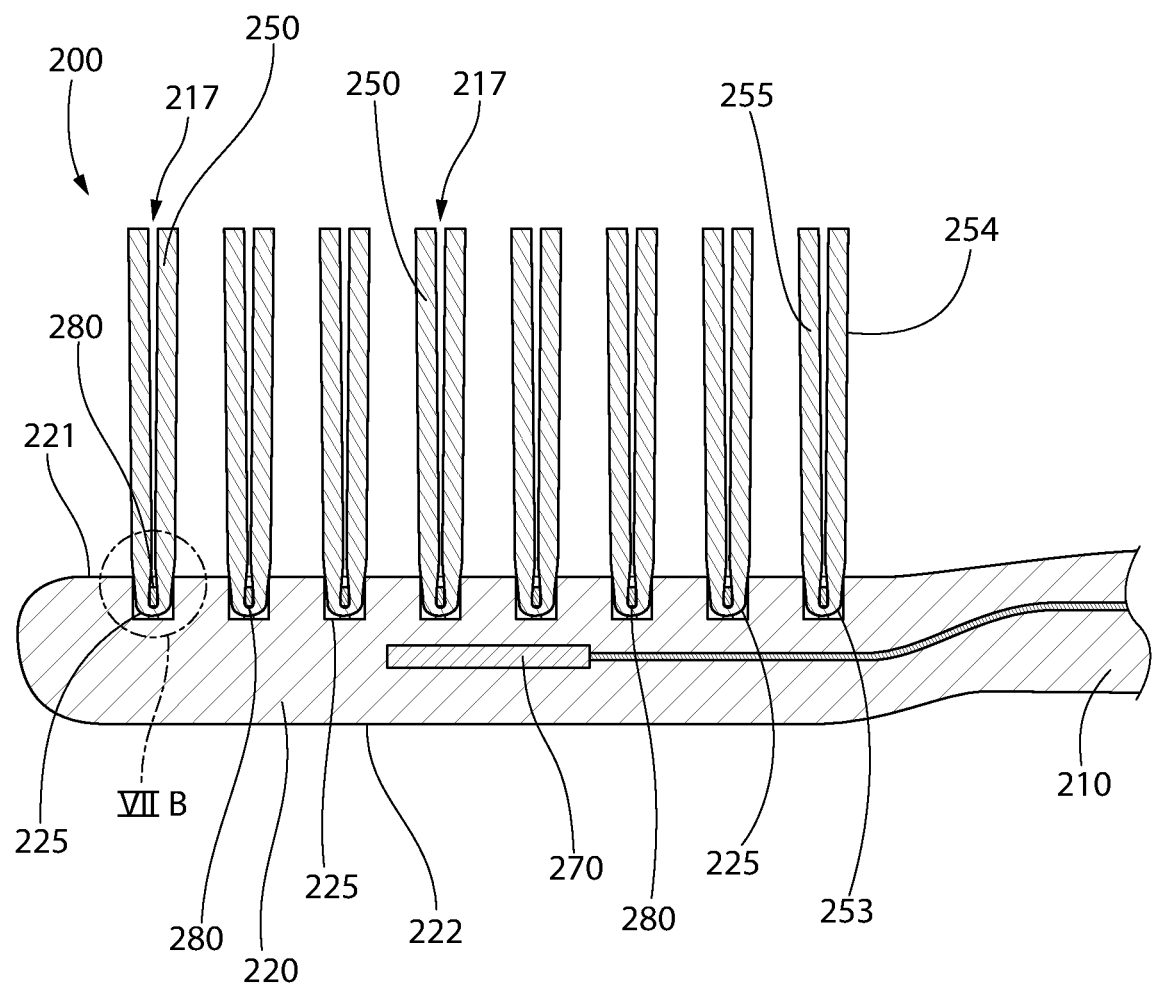
FIG. 7A is a cross-sectional view taken along line VA-VA of FIG. 1 wherein the light-transmitting filaments of FIG. 6 are coupled to a head of the oral care implement.
Figure 7B:
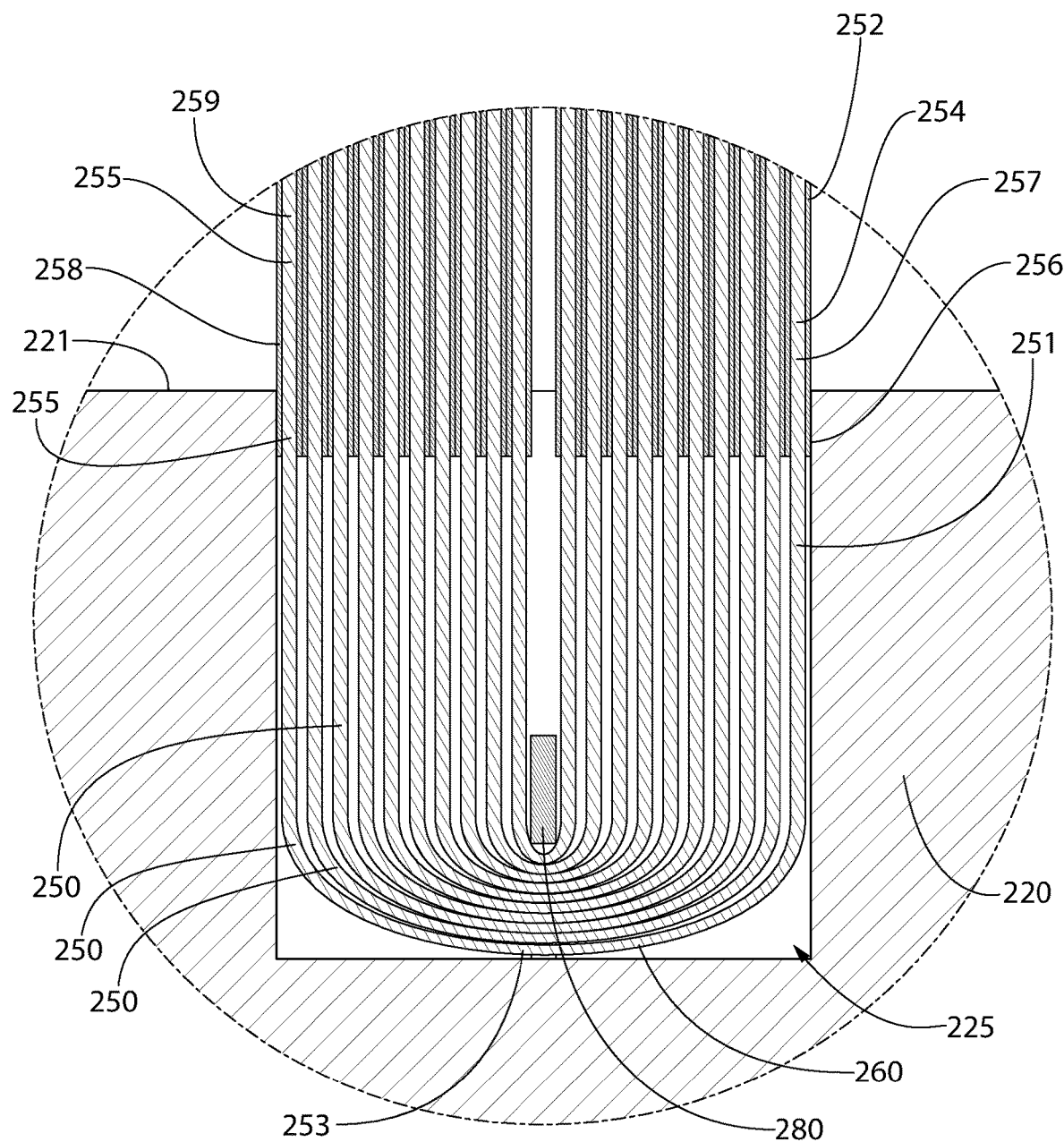
FIG. 7B is a close-up view of area VIIB of FIG. 7A.

Referring to FIGS. 7A and 7B concurrently, an oral care implement 200 is illustrated and will be described in accordance with an embodiment of the present invention. The oral care implement 200 is similar to the oral care implement 100 except as described herein below. Specifically, the oral care implement 200 uses staple technology to couple the light-transmitting filaments 250 to the oral care implement 200 rather than the anchor-free tufting techniques (i.e., melting/fusing the base portions 157 of the light-transmitting filaments together).

The oral care implement 200 comprises a handle 210 and a head 220. In this embodiment, the head 220 is a single piece structure that is integrally formed with the handle 210 and there is no separately formed plate. The head 220 comprises a front surface 221 and an opposing rear surface 222. A plurality of tuft holes 225 are formed into the front surface 221 of the head 220. The tuft holes 225 may be referred to herein as a passageway in the head 220 or body that terminates in an aperture or opening in a front surface 221 of the head 220 or body. A plurality of the light-transmitting filaments 250 are clumped together into one or more tufts 217 and the light-transmitting filaments 250 of each tuft 217 are inserted into one of the tuft holes 225 such that the bight portions 253 of the light-transmitting filaments 250 are positioned within the tuft holes 225. The tufts 217 are then secured to the head 220 by a staple 280. Specifically, the staple 280 is secured within each tuft hole 225 adjacent or in contact with the top of the bight portions 253 so that the light-transmitting filaments 250 and the tufts 217 are securely coupled to the head 220 within the respective tuft hole 225.

The oral care implement 200 of this embodiment includes a light source 270 that is similar to the light source 170 of the oral care implement 100 described above. The light source 270 is positioned in operable cooperation with the light-transmitting filaments 250 to emit the light into and through the light-transmitting filaments 250. Specifically, in this embodiment the bight portions 253 of the light-transmitting filaments 250 may collectively be considered the anchor portion of the tuft 217. The light source 270 generates light that is transmitted through the bight portions 253 of the light-transmitting filaments 250 and through the core component 251 (i.e., through the first and second sections 257, 259 of the core component 251). The light is then emitted from the light-emitting portions 264, 265 of the first and second sections 257, 259 of the core component 251.

Referring to FIGS. 8A-8E, a method of forming a light-emitting oral care implement will be described in accordance with an embodiment of the present invention. First, referring to FIG. 8A, a plurality of filaments 300 are formed, each of the filaments 300 comprising a core component 301 formed of a first material having a first light transmittance and a sheath component 302 formed of a second material having a second light transmittance. In the exemplified embodiment the sheath component 302 surrounds the core component 301 along its entire length. As discussed above, the first light transmittance of the first material that forms the core component 301 is greater than the second light transmittance of the second material that forms the sheath component 302.

Figures 8A, 8B:
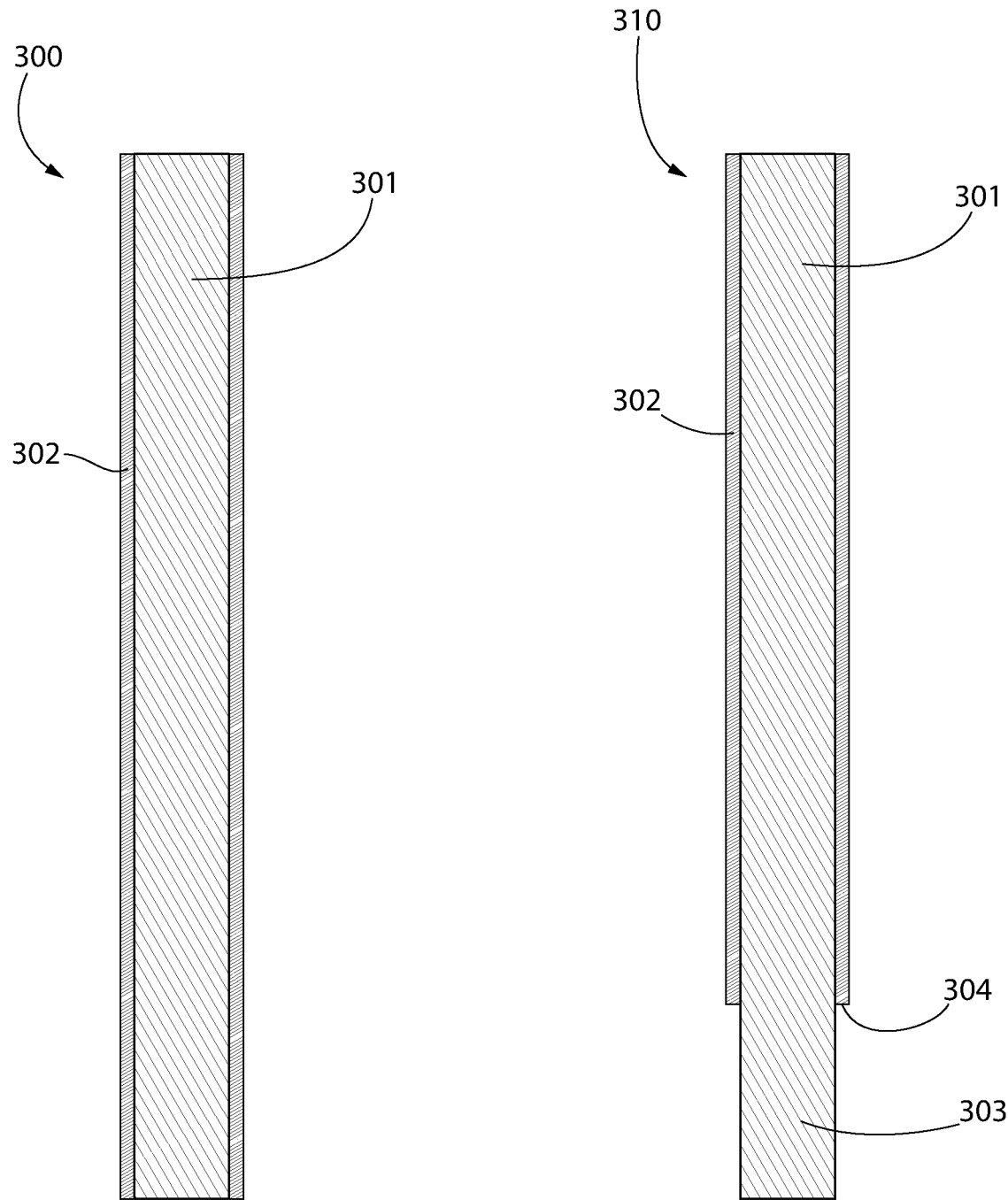
FIG. 8A is a cross-sectional view of one of the light-transmitting filaments of FIG. 3 having a core component and a sheath component.
FIG. 8B is a cross-sectional view of the light-transmitting filament of FIG. 8A with a portion of the sheath component removed.
Figure 8C:
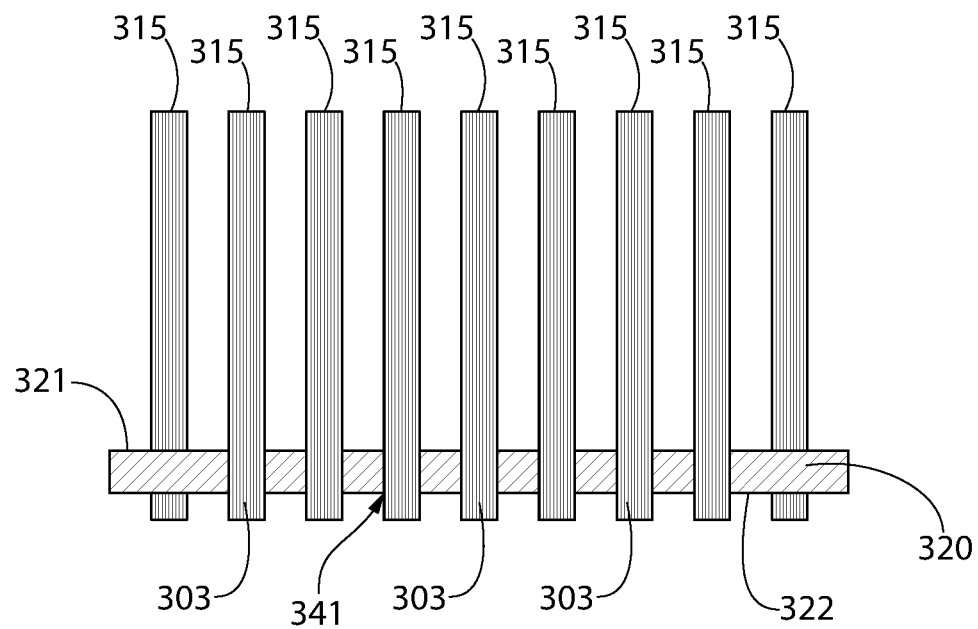
FIG. 8C is a cross-sectional view illustrating a plurality of the light-transmitting filaments of FIG. 8B arranged in tufts and inserted through holes in a plate.

Next, referring to FIG. 8B, for each of the filaments 300, a portion of the sheath component 302 is removed so that a base portion 303 of the core component 301 is exposed and no longer surrounded by the sheath component 302. Specifically, a lower portion of the sheath component 302 is removed such that the base portion 303 of the core component 301 protrudes from a lower end 304 of a remaining portion of the sheath component 302. Removing the lower portion of the sheath component 302 forms a light-transmitting filament 310, depicted in FIG. 8B.

In certain embodiments, the portion of the sheath component 302 may be removed by eroding the portion of the sheath component 302 with a chemical etchant. Specifically, in certain embodiments, the second material of the sheath component 302 may be erodible by a chemical etchant and the first material of the core component 301 may be resistant to the chemical etchant. In this embodiment, the filaments 300 may be partially dipped in the chemical etchant so that the portion of the sheath component 302 is removed or eroded by the chemical etchant. The core component 301 will remain unaffected by the chemical etchant because the first material is resistant thereto. Of course, using a chemical etchant is only one technique for forming the light-emitting filament 310. In other embodiments the portion of the sheath component 302 may be removed using a cutting or shearing element. In other embodiments the light-transmitting filament 310 may be formed by an extrusion process so that removal of a portion of the sheath component 302 is not required. Other processes and techniques are possible and within the scope of the present invention.

Next, referring to FIG. 9C, the light-transmitting filaments 310 are bundled into filament bundles 315 (also referred to herein as tufts) while maintaining the base portions 303 of the core components 301 adjacent to one another. The filament bundles 315 are then inserted into a passageway 341 of a body of a light-emitting oral care implement. Specifically, referring to FIG. 9C, the filament bundles 315 are inserted into holes or passageways 341 that are formed through a plate 320 so that the base portions 303 of the core components 301 protrude from a rear or bottom surface 322 of the plate 320. The holes or passageways extend through the entirety of the plate 320 from a front surface 321 of the plate 320 to the rear surface 322 of the plate 320.

Figure 8D:
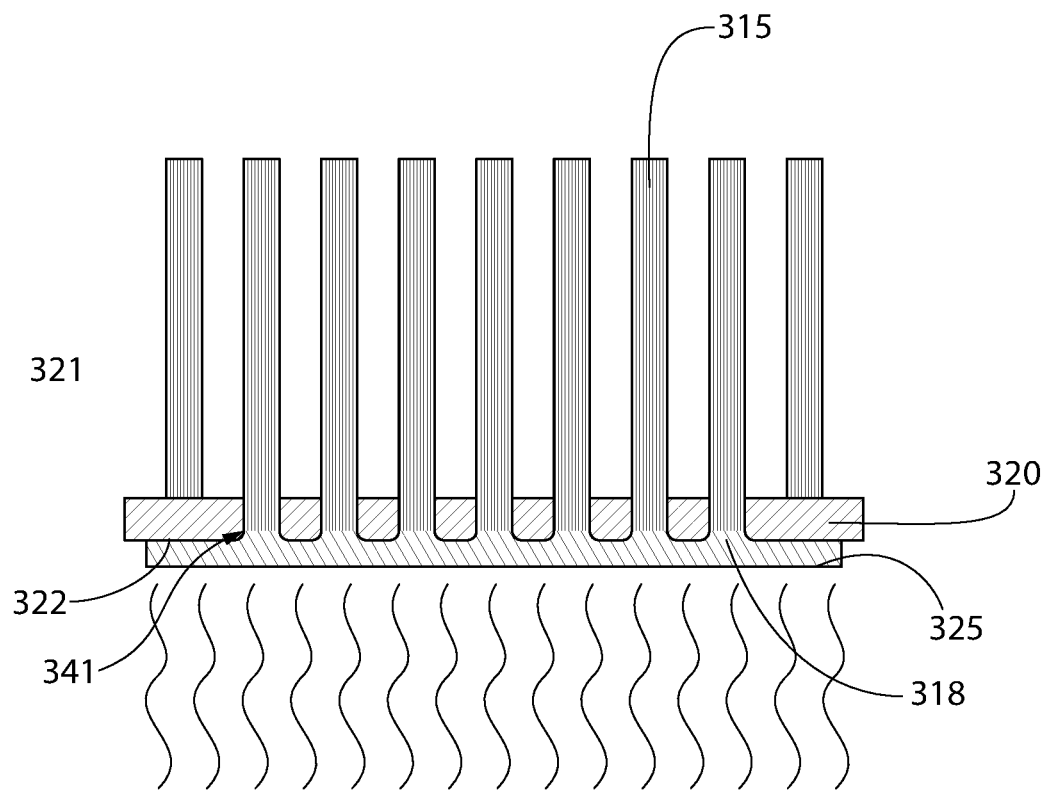
FIG. 8D is a cross-sectional view illustrating the application of heat to base portions of the core components of the light-transmitting filaments to form a matte.

Next, referring to FIG. 8D, the base portions 303 of the core components 301 of the light-transmitting filaments 310 of the filament bundles 315 are anchored within the body or plate 320 to facilitate mounting or coupling the light-transmitting filaments 310 to the oral care implement. Specifically, in the exemplified embodiment this is accomplished by fusing the base portions 303 of the light-transmitting filaments 310 of the bundle 315 together to form a monolithic mass of the first material (i.e., a matte 325) that is free of the second material. Specifically, because the base portions 303 of the light-transmitting filaments 310 are formed entirely of the core component 351 and entirely of the first material, the monolithic mass of the matte 325 is also formed entirely of the first material of the core component 351. Fusing the base portions 303 of the light-transmitting filaments 310 of the bundle 315 together is achieved by applying heat, ultrasonic energy, or the like to the base portions 303 of the light-transmitting filaments 310 of the filament bundle 315. Of course, as discussed above in other embodiments the light-transmitting filaments 310 may be anchored to the oral care implement by using a staple.

Figure 8E:
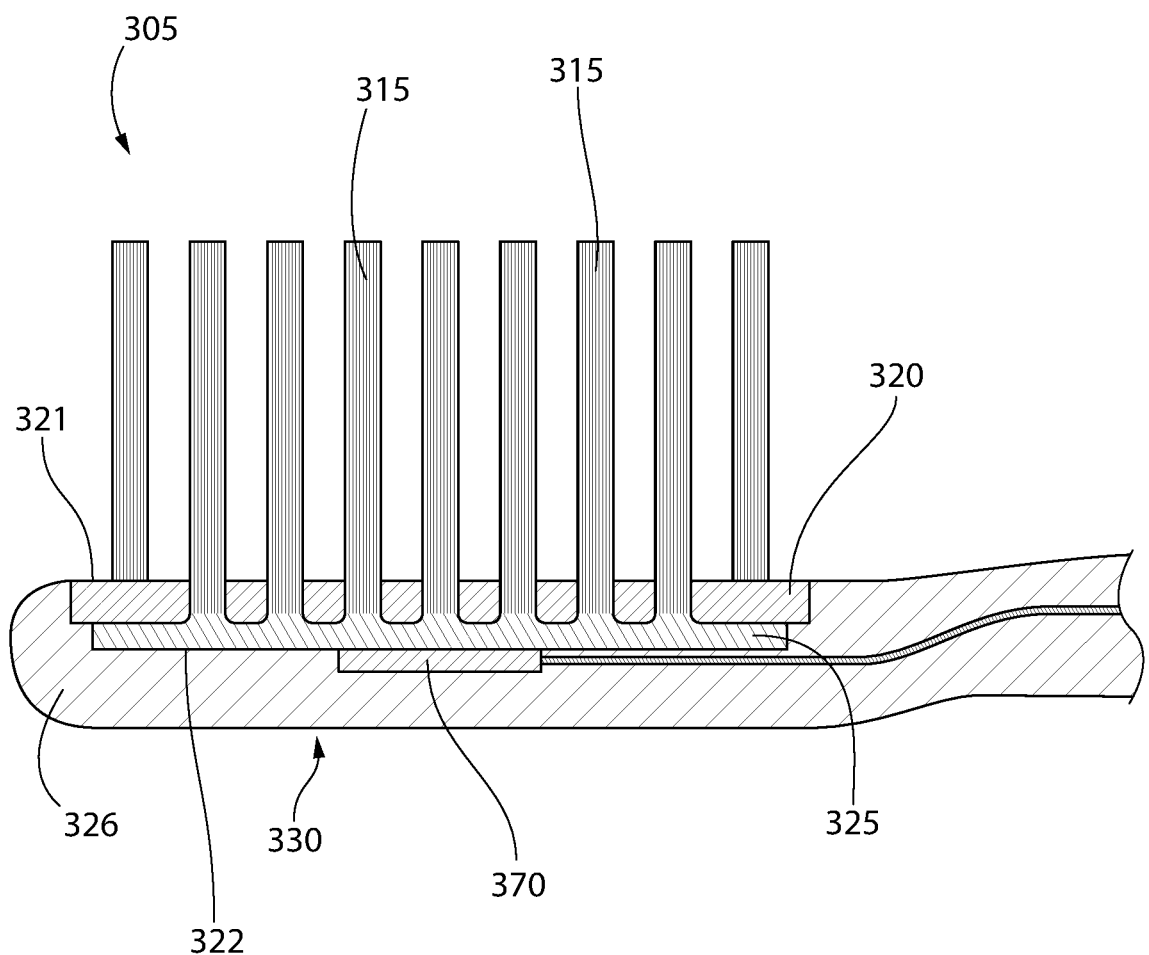
FIG. 8E is a cross-sectional view illustrating the plate coupled to a body of an oral care implement.

Referring to FIG. 8E, in the final step of the exemplified embodiment, the plate 320 with the filament bundles 315 coupled thereto is coupled to a support 326 of a head 330 of an oral care implement 305. The plate 320 is coupled to the support 326 so that a light source 370 is in operable cooperation with the light-transmitting filaments 310 to facilitate transmitting light through the light-transmitting filaments 310 and emitting the light from the distal ends of the light-transmitting filaments 310 as described herein above.

Although the method has been described with regard to using an anchor-free tufting, the method of forming a light-transmitting oral care implement can also be accomplished using anchor or staple technology which has been described herein with reference to FIGS. 7A and 7B.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:
1. A light-emitting oral care implement comprising:
a body having a front surface;
a light delivery unit comprising:
   a passageway in a portion of the body that terminates in an aperture in the front surface of the body;
   a tuft comprising a plurality of light-transmitting filaments, each of the light-transmitting filaments comprising:
      a core component formed of a first material having a first transmittance;
      a sheath component formed of a second material having a second transmittance, the sheath component surrounding the core component, the first transmittance being greater than the second transmittance; and the core component comprising a base portion that protrudes from a lower end of the sheath component;

the tuft mounted within the passageway and comprising an anchor portion that anchors the tuft to the body, the base portions of the light-transmitting filaments forming the anchor portion; and a light source in operable cooperation with the anchor portion of the tuft such that light generated by the light source is transmitted through the anchor portion of the tuft, through the core components of the light-transmitting filaments of the tuft, and emitted from the light-transmitting filaments of the tuft at a location above the front surface of the body;

wherein for each of the light-transmitting filaments, the core component comprises a light-emitting portion that is exposed at a distal end of the light-transmitting filament;

wherein the light generated by the light source is emitted from the light-transmitting filament via the light-emitting portion; and wherein for each of the light-transmitting filaments, the light-emitting portion of the core component protrudes from an upper end of the sheath component.

2. The oral care implement according to claim 1 wherein the anchor portion is a monolithic mass of the first material formed by the base portions of the light-transmitting filaments of the tuft being fused together.

3. The oral care implement according to claim 2 wherein the anchor portion is substantially free of the second material.

4. The oral care implement according to claim 2 further comprising:

a plurality of the light delivery units;

the anchor portions of the plurality of the light delivery units fused together to collectively form a matte of the first material; and the light source in operable cooperation with the matte such that light generated by the light source is transmitted through the matte, through the core components of the light-transmitting filaments of the tuft of each of the plurality of the light delivery units, and emitted from the light-transmitting filaments of the tuft of each of the plurality of the light delivery units at a location above the front surface of the body.

5. The oral care implement according to claim 4 further comprising:

the body comprising a handle and a head, the head comprising the portion of the body;

the portion of the body comprising a plate comprising the front surface of the body and a rear surface opposite the front surface;

for each of the plurality of the light delivery units, the passageway extending through the plate from the front surface to the rear surface; and wherein the matte is located adjacent the rear surface.

6. The oral care implement according to claim 5 wherein the head comprises a support, the plate coupled to the support to form an internal cavity, the matte and the light source disposed within the internal cavity.

7. The oral care implement according to claim 1 wherein each of the light-transmitting filaments is a U-shaped filament comprising a bight portion, a first leg portion extending from the bight portion, and a second leg portion extending from the bight portion; and wherein for each of the light-transmitting filaments: (1) the first leg portion comprises a first section of the sheath component and a first section of the core component, the first section of the sheath component surrounding the first section of the core component; (2) the second leg portion comprises a second section of the sheath component and a second section of the core component, the second section of the sheath component surrounding the second section of the core component; and (3) the bight portion comprising a third section of the core component, the third section of the core component protruding from lower ends of the first and second sections of the sheath component.

8. The oral care implement according to claim 7 further comprising:

wherein for each of the light-transmitting filaments: (1) the first section of the core component comprises a light-emitting portion that is exposed at a distal end of the first leg portion; and (2) the second section of the core component comprises a light-emitting portion that is exposed at a distal end of the second leg portion; and wherein for each of the light-transmitting filaments, the light generated by the light source is emitted from the light-transmitting filament via the light-emitting portions of the first and second sections of the core component.

9. The oral care implement according to claim 7 further comprising:

a plurality of the light delivery units;

the body comprising a handle and a head, the head comprising the portion of the body; and for each of the plurality of the light delivery units, the tuft anchored in the passageway by a staple.

10. The oral care implement according to claim 1 wherein each of the light-transmitting filaments is a U-shaped filament comprising a bight portion, a first leg portion extending from the bight portion, and a second leg portion extending from the bight portion; and wherein for each of the light-transmitting filaments, the bight portion is formed by the core component and is free of the sheath component.

11. The oral care implement according to claim 1 wherein the second material is opaque and the first material is translucent or transparent.

12. The oral care implement according to claim 1 wherein the second material is erodible by a chemical etchant and the first material is resistant to the chemical etchant.

13. A light-emitting toothbrush comprising:

a handle;

a head having a front surface and a plurality of tuft holes;

a plurality of bristle tufts mounted to the head within the plurality of tuft holes, the plurality of bristle tufts protruding from the front surface of the head to form a tooth cleaning element field;

the plurality of bristle tufts comprising at least one light-transmitting tuft comprising a plurality of light-transmitting filaments, each of the light-transmitting filaments comprising:

a core component formed of a first material having a first transmittance;

a sheath component formed of a second material having a second transmittance, the sheath component surrounding the core component, the first transmittance being greater than the second transmittance; and the core component comprising a base portion that protrudes from a lower end of the sheath component;

the at least one light-transmitting tuft comprising an anchor portion embedded in the head that is formed by the base portions of the light-transmitting filaments, the anchor portion formed of the first material and free of the second material; and a light source in operable cooperation with the anchor portion of the at least one light-transmitting tuft.

14. The oral care implement according to claim 13 wherein the anchor portion is a monolithic mass of the first material formed by the base portions of the light-transmitting filaments of the at least one light-transmitting tuft being fused together.

15. A method of forming a light-emitting oral care implement, the method comprising:
   a) forming a plurality of filaments comprising: a core component formed of a first material having a first light transmittance; and a sheath component formed of a second material having a second light transmittance, the sheath component surrounding the core component, the first light transmittance being greater than the second light transmittance;
   b) for each of the filaments, removing a portion of the sheath component so that a base portion of the core component is exposed and protrudes from a lower end of a remaining portion of the sheath component, thereby forming a plurality of light-transmitting filaments;
   c) mounting the plurality of light-transmitting filaments to a body of the light-emitting oral care implement; and
   d) operably coupling a light source to the base portions of the plurality of light-transmitting filaments within the body;
      wherein for each of the plurality of filaments, the core component having a light emitting portion that protrudes from an upper end of the sheath component.

16. The method according to claim 15 further comprising: wherein step c) comprises:
   c-1) bundling the light-transmitting filaments into a filament bundle such that the base portions of the light-transmitting filaments are adjacent one another;
   c-2) inserting the filament bundle into a passageway of the body of the light-emitting oral care implement; and
   c-3) anchoring the base portions of the light-transmitting filaments of the filament bundle within the body.

17. The method according to claim 16 wherein step c-3) comprises fusing the base portions of the light-transmitting filaments of the filament bundle together to form a monolithic mass of the first material, the monolithic mass being substantially free of the second material.

* * * * *